United States Patent
Ernst et al.

(10) Patent No.: US 10,216,698 B2
(45) Date of Patent: Feb. 26, 2019

(54) ANALYSIS DEVICE INCLUDING A MEMS AND/OR NEMS NETWORK

(75) Inventors: Thomas Ernst, Morette (FR); Philippe Andreucci, Moirans (FR); Eric Colinet, Grenoble (FR); Laurent Duraffourg, Voiron (FR); Edward B. Myers, Burbank, CA (US); Michael L. Roukes, Pasadena, CA (US)

(73) Assignees: Commissariat à l 'Energie Atomique et aux Energies Alternatives, Paris (FR); California Institute of Technology, Pasadena, CA (US)

( * ) Notice: Subject to any disclaimer, the term of this patent is extended or adjusted under 35 U.S.C. 154(b) by 1397 days.

(21) Appl. No.: 13/702,790

(22) PCT Filed: Jun. 6, 2011

(86) PCT No.: PCT/EP2011/059305
§ 371 (c)(1),
(2), (4) Date: Feb. 20, 2013

(87) PCT Pub. No.: WO2011/154363
PCT Pub. Date: Dec. 15, 2011

(65) Prior Publication Data
US 2013/0144542 A1    Jun. 6, 2013

Related U.S. Application Data

(60) Provisional application No. 61/352,248, filed on Jun. 7, 2010.

(51) Int. Cl.
*G06F 17/00* (2006.01)
*B81C 1/00* (2006.01)
*G01N 30/60* (2006.01)

(52) U.S. Cl.
CPC .......... *G06F 17/00* (2013.01); *B81C 1/00238* (2013.01); *B81B 2201/06* (2013.01);
(Continued)

(58) Field of Classification Search
CPC ....... G01N 30/6095; G01N 2291/0256; G01N 30/60; G01N 2030/60; G01N 30/72
See application file for complete search history.

(56) References Cited

U.S. PATENT DOCUMENTS 4,547,748 A * 10/1985 Ballato ................... H03B 5/32
310/320
5,544,276 A * 8/1996 Loux ....................... F24H 1/105
137/341
(Continued)

FOREIGN PATENT DOCUMENTS

JP    11-67820 A    3/1999
JP    2002-524755   8/2002
(Continued)

OTHER PUBLICATIONS

U.S. Appl. No. 14/619,656, filed Feb. 11, 2015, Ruellan et al.
(Continued)

*Primary Examiner* — Harshad R Patel
*Assistant Examiner* — Tran M Tran
(74) *Attorney, Agent, or Firm* — Oblon, McClelland, Maier & Neustadt, L.L.P.

(57) ABSTRACT

A device for analyzing a fluid, including a layer including a plurality of sensors of MEMS and/or NEMS type, a layer including a mechanism controlling the sensor and for processing information transmitted by the sensors, the control and processing mechanism being electrically connected to the detectors, and a layer positioned on the layer including
(Continued)

the sensors on a side of a face including the sensors including a mechanism spatially and temporally distributing the fluid on the sensors.

21 Claims, 8 Drawing Sheets

(52) U.S. Cl.
CPC .............. *B81C 2203/0771* (2013.01); *B81C 2203/0792* (2013.01); *G01N 30/6095* (2013.01); *G01N 2291/0256* (2013.01); *Y10T 29/49117* (2015.01)

(56) References Cited

U.S. PATENT DOCUMENTS

| | | | | |
|---|---|---|---|---|
| 5,989,445 A * | 11/1999 | Wise | ............... | A61M 5/32 216/2 |
| 5,992,769 A * | 11/1999 | Wise | ............... | A61M 5/32 239/135 |
| 6,068,780 A * | 5/2000 | Yu | ............... | G01N 30/6095 216/10 |
| 6,127,908 A * | 10/2000 | Bozler | ............... | B81B 3/0021 330/66 |
| 6,193,501 B1 * | 2/2001 | Masel | ............... | F23C 13/00 422/177 |
| 6,313,529 B1 * | 11/2001 | Yoshihara | ............... | H01L 23/10 257/724 |
| 6,575,020 B1 | 6/2003 | de Charmoy Grey et al. | | |
| 6,646,525 B2 * | 11/2003 | Bozler | ............... | B81B 3/0021 330/66 |
| 6,732,567 B2 * | 5/2004 | Briscoe | ............... | F04B 19/006 73/23.2 |
| 6,838,640 B2 * | 1/2005 | Wise | ............... | G01N 30/30 219/201 |
| 6,855,251 B2 * | 2/2005 | Moon | ............... | G01N 30/6095 210/198.2 |
| 6,893,885 B2 * | 5/2005 | Lemmerhirt | ............... | B81C 3/008 219/209 |
| 6,936,491 B2 * | 8/2005 | Partridge | ............... | B81C 1/00301 438/48 |
| 7,008,193 B2 * | 3/2006 | Najafi | ............... | F04B 45/047 417/244 |
| 7,223,366 B2 * | 5/2007 | Hauan | ............... | G01N 29/036 422/50 |
| 7,253,488 B2 * | 8/2007 | Zhan | ............... | B81B 3/0021 257/414 |
| 7,311,009 B2 * | 12/2007 | Kotovsky | ............... | G01L 1/18 438/50 |
| 7,352,040 B2 * | 4/2008 | Partridge | ............... | B81C 1/00301 257/419 |
| 7,449,758 B2 * | 11/2008 | Axelrod | ............... | G01N 29/036 257/415 |
| 7,550,810 B2 * | 6/2009 | Mignard | ............... | B81B 3/0078 257/415 |
| 7,608,818 B2 * | 10/2009 | Miller | ............... | G01N 27/624 250/281 |
| 7,692,141 B2 * | 4/2010 | Tai | ............... | G01N 30/6095 210/748.01 |
| 7,703,313 B2 * | 4/2010 | Higashi | ............... | B01L 3/5027 216/2 |
| 7,785,912 B2 * | 8/2010 | Zhan | ............... | B81B 3/0021 438/52 |
| 8,029,863 B2 * | 10/2011 | Fonverne | ............... | B01J 19/0093 427/249.1 |
| 8,087,283 B2 * | 1/2012 | Wang | ............... | A61B 5/082 73/23.4 |
| 8,132,443 B2 * | 3/2012 | McGill | ............... | B01J 20/205 73/23.39 |
| 8,431,080 B2 * | 4/2013 | Liu | ............... | B01L 3/502707 257/417 |
| 8,558,250 B2 * | 10/2013 | Venugopal | ............ | G01L 19/083 257/415 |
| 8,646,335 B2 * | 2/2014 | Kotovsky | ............... | G01L 1/18 438/51 |
| 8,692,337 B2 * | 4/2014 | Berthelot | ............... | B81C 3/008 257/415 |
| 8,695,401 B2 * | 4/2014 | Wang | ............... | A61B 5/082 422/89 |
| 8,707,734 B2 * | 4/2014 | Haque | ............... | C03C 19/00 65/36 |
| 8,820,140 B2 * | 9/2014 | Puget | ............... | G01N 30/60 73/23.39 |
| 8,946,831 B2 * | 2/2015 | Liu | ............... | B81B 3/0078 257/414 |
| 8,999,245 B2 * | 4/2015 | Wang | ............... | G01N 30/30 422/70 |
| 9,014,796 B2 * | 4/2015 | Kipke | ............... | A61B 5/04001 600/544 |
| 9,035,364 B2 * | 5/2015 | Chang | ............... | H01L 29/7869 257/288 |
| 9,234,879 B2 * | 1/2016 | Ollier | ............... | B81C 1/00119 |
| 9,340,410 B2 * | 5/2016 | Ollier | ............... | B81B 7/0061 |
| 2003/0175947 A1 * | 9/2003 | Liu | ............... | B01F 11/0071 435/288.5 |
| 2004/0067008 A1 * | 4/2004 | Tai | ............... | G02F 1/31 385/16 |
| 2004/0087008 A1 | 5/2004 | Schembri | | |
| 2006/0071286 A1 | 4/2006 | Axelrod et al. | | |
| 2007/0023621 A1 * | 2/2007 | Blick | ............... | B82Y 15/00 250/251 |
| 2007/0172940 A9 * | 7/2007 | Manalis | ............ | B01L 3/502707 435/287.2 |
| 2009/0084496 A1 * | 4/2009 | Fonverne | ............ | B01J 19/0093 156/292 |
| 2010/0018864 A1 * | 1/2010 | Sarrut | ............... | B01L 3/502707 204/601 |
| 2010/0019393 A1 | 1/2010 | Hsieh et al. | | |
| 2010/0297781 A1 | 11/2010 | Scheurle | | |
| 2013/0061459 A1 | 3/2013 | Morin et al. | | |
| 2013/0125621 A1 | 5/2013 | Puget et al. | | |

FOREIGN PATENT DOCUMENTS

| | | |
|---|---|---|
| JP | 2004-163427 A | 6/2004 |
| JP | 2004-533605 A | 11/2004 |
| JP | 2005-201682 A | 7/2005 |
| JP | 2007-506977 A | 3/2007 |
| JP | 2008-78475 A | 4/2008 |
| JP | 2009-502531 A | 1/2009 |
| JP | 2009-105411 A | 5/2009 |
| JP | 2009-542452 A | 12/2009 |
| JP | 2010-44066 A | 2/2010 |
| JP | 2011-524536 A | 9/2011 |
| WO | WO 02/072264 A1 | 9/2002 |
| WO | WO 2007/018955 A1 | 2/2007 |
| WO | WO 2009/155125 A1 | 12/2009 |

OTHER PUBLICATIONS

Office Action dated Feb. 23, 2015 in Japanese Patent Application No. 2013-513654 (with English language translation).
Office Action dated Jan. 8, 2016 in Japanese Patent Application No. 2013-513654 (with English language translation).
U.S. Appl. No. 13/702,226, filed Apr. 17, 2013, Ernst et al.
International Search Report dated May 11, 2012, in International Application No. PCT/EP 2011/059305.
Jian-Qiang Lu, "3-D Hyperintegration and Packaging Technologies for Micro-Nano Systems", Proceedings of the IEEE, vol. 97, No. 1, XP011252769, Jan. 1, 2009, pp. 18-30.
Bioh Kim, et al., "Advanced Wafer Bonding Solutions for TSV Integration with Thin Wafers", IEEE International Conference on 3D System Integration, 2009, 6 pages.
Perceval Coudrain, et al., "Setting up 3D Sequential Integration for Back-Illuminated CMOS Image Sensors with highly Miniaturized Pixels with low temperature fully Depleted SOI transistors", Electron Devices Meeting, IEDM, 2008, 4 pages.

(56) References Cited

OTHER PUBLICATIONS

D.Henry, et al., "Development and characterization of high electrical performances TSV for 3D applications", Electronics Packaging Technology Conference, 2009, EPTV 09, $11^{th}$, pp. 528-535.

Ayman El-Faramawy, et al., "Efficiency of Nano-Electrospray Ionization", American Society for Mass Spectrometry, 2005, 16, 6 pages.

Bradley C. Kaanta, et al., "A monolithically fabricated gas chromatography separation column with an integrated high sensitivity thermal conductivity detector", Journal of Micromechanics and Microengineering, 2010, 20(5), 6 pages.

Office Action dated Jul. 24, 2017 in Japanese Patent Application No. 2016-198045 (with English language translation).

European communication dated Dec. 10, 2018 in EP Patent Application No. 11 725 674.3-1020.

Boisen A. et al: "Design & fabrication of canntilever array biosensors", Materials Today, Elsevier, Amsterdam, NL, vol. 12, No. 9, Sep. 1, 2009 (Sep. 1, 2009), pp. 32-38, XP026644069, ISSN: 1369-7021, DOI: 10.1018/S1369-7021 (09)70249-4 [retrieved on Sep. 1, 2009].

Whiting J. J. et al: "High-speed two-dimensional gas chromatography using microfabricated GC columns combined with nanoelectromechanical mass sensors", Transducers 2009: 2009 International Solid-State Sensors, Actuators and Microsystems Conference: Denver, Colorado, USA, Jun. 21-25, 2009, IEEE, Piscataway, NJ, USA, Jun. 21, 2009 (June. 21, 2009), pp. 1666-1669, XP031545662, ISBN: 978-1-4244-4190-7.

\* cited by examiner

ANALYSIS DEVICE INCLUDING A MEMS AND/OR NEMS NETWORK

TECHNICAL AND PRIOR ART

The present invention relates to a device for analyzing one or more characteristics of an outside environment. This outside environment may for example be a fluid to be analyzed comprising one or more species, the characteristics for example being its qualitative and quantitative composition. The analysis device applies networks of sensors formed by micro-electromechanical system (MEMS) and/or by nano-electromechanical systems (NEMS).

In order to improve compactness of integrated circuits, increasing the integration density of the electronic components and of the electric interconnections which are part of these integrated circuits is sought.

One way for increasing this integration density is to make three-dimensional integrated circuits, i.e. including several electronic levels superposed onto each other, one level including control transistors, one level including MEMS or NEMS systems, and optionally a level inserted between the two levels described previously including conductive lines and columns connecting the MEMS and/or NEMS systems to the control transistors.

Three-dimensional integration examples are described in document«3-D Hyperintegration and Packaging Technologies for Micro-Nano Systems»of J. Q. LU, Proceedings of the IEEE, Vol. 97, No. 1, January 2009.

This document also describes a three-dimensional device including a plurality of MEMS or NEMS systems on a surface. However this device does not draw any benefit from this network of MEMS or NEMS systems.

Therefore an object of the present invention is to propose a compact electronic device including a network of MEMS and/or NEMS systems, benefiting from this network of micro- and/or nano-electromechanical systems.

DISCUSSION OF THE INVENTION

The object stated earlier is achieved by an analysis device including a level comprising a plurality of MEMS and/or NEMS systems forming sensors, a level including means for controlling said sensors individually or per group and for processing information sent by the sensors, and an additional level positioned on the sensors, including means for distributing at least one stimulus of the environment to be analyzed by the sensors, said means ensuring distribution of this stimulus on each sensor or group of sensors in a determined way in time and in space.

In other words, according to the invention, the putting into contact of said at least one stimulus with the sensors is under control in order to benefit from their large number.

For this, the means for encapsulating MEMS or NEMS systems participate in the controlled distribution of said at least one stimulus of the environment to be analyzed by the detectors.

The putting into contact with all the sensors may either be simultaneous or successive. In the case when the environment is a fluid, the stimulus is for example formed by molecules, for which the intention is to determine the type and/or concentration.

For example and in a particularly advantageous way, a gas chromatography column may be made having great compactness, the environment either being a gas such as an air sample, or a liquid which will be vaporized upon its entering the column, the distribution means comprising at least one channel causing circulation of the fluid over a path of sensors. In this example, the fluid circulates on the sensors positioned behind each other, successively coming into contact with the sensors.

In the case of a mass spectrometer, the distribution means may be injectors of the fluid on the sensors, for example protein molecules.

The injectors ensure injection as close as possible to the sensors avoiding too large spatial dispersion of the molecules.

In the case of a device for determining the type of cells, the distribution means may for example bring cells onto each sensor, the sensors being intended to conduct force measurements. By means of the invention, the molecules are brought onto all the sensors simultaneously, which allows a substantial increase in the analysis throughput.

The subject-matter of the present invention is then a device for analyzing an environment, including:
  a layer provided with a plurality of sensors of the MEMS and/or NEMS type respectively including at least one mobile component capable of reacting to a stimulus,
  a layer including means for controlling the sensors and for treating information transmitted by the sensors, said control and processing means being electrically connected to the sensors, and
  a layer positioned on the layer on the side of the face including the sensors including means for spatially and temporally distributing the stimulus or stimuli to said sensors.

In an embodiment, the distribution means distribute the stimulus or stimuli simultaneously or quasi simultaneously onto all the sensors (2) or group of sensors (2). The distribution of the stimulus or stimuli on the sensors may be quasi simultaneous, since a slight time shift may appear depending on the position of the sensors in the network.

In another embodiment, the distribution means distribute the stimulus or stimuli in a time-shifted way onto a succession of given sensors.

The environment is for example a fluid, the distribution means may then include at least one channel for which one end, a so-called inlet end, is intended to be connected to a supply of the fluid to be analyzed. The distribution layer may then include means for filtering certain compounds contained in said fluid.

The analysis device according to the present invention may form a mass spectrometer, wherein the sensors form resonators and in which the distribution means include means for injecting and/or ionizing said fluid on a sensor or a group of sensors, said at least one channel including a second end connected to the injection and/or ionization means.

The injection means are formed for example by at least one injector of the electrospray ionization type.

Alternatively, the distribution means are formed by a plurality of channels intended to deliver fluid containing cells to each of the sensors, the second so-called outlet end of each of the channels opening out above a sensor or a group of sensors, said sensors forming sensors for the forces applied by the cells on the mobile component of the sensors.

In another embodiment where the distribution means distribute the stimulus or stimuli in a time-shifted way onto a succession of given sensors and the environment is a fluid, the distribution means may include a channel and form a gas chromatography micro-column.

The channel of the distribution means for example includes at least one groove made in the distribution layer, the open end of the groove covering said succession of given sensors, so that the fluid circulating in the groove comes into contact with said succession of given sensors. Said at least one groove advantageously includes at least one stationary phase. The sensors are also preferably chemically functionalized by depositing at least one material providing a certain affinity with the species to be separated from the fluid to be analyzed.

The sensors may be functionalized with different materials and have identical or different forms in the network of the device.

Advantageously, the interval between the sensors is less than half of the width of a detection peak.

The analysis device according to the present invention may include an interconnection layer between the layer of sensors and the layer including the control and processing means, said interconnection layer electrically connecting the sensors to the control and processing means.

In an exemplary embodiment, the layer providing with the control and processing means may be divided into interconnected first and second sublayers, the first sublayer including near-pixel basic electronics for analog preprocessing of each sensor, and the second sublayer including electronics capable of achieving digital processing of the information.

The subject-matter of the present invention is also a method for manufacturing a device according to the present invention by three-dimensional integration including the steps:

making the layer provided with sensors,
making the layer provided with control and processing means,
superposing said layers and interconnecting the control and processing means and the sensors,
making the distribution layer,
transferring the distribution layer in the front face of the layer provided with the sensors.

In an embodiment, interconnection of the control and processing means and of the sensors is achieved by wire bonding.

In another embodiment, interconnection of the control and processing means and of the sensors is achieved by an interconnection layer interposed between the layer provided with the control and processing means and the layer provided with the sensors.

A manufacturing method according to the present invention may include the steps of:

making at least one electronic circuit of the MOS type and/or at least one level of electrical interconnections on a substrate,
uniformly implanting dopants in at least one portion of a layer of an SOI substrate,
thermally activating dopants implanted in the portion of the layer of the SOI substrate,[2]
transferring the SOI substrate layer onto the substrate provided with the electronic circuit,
thinning the SOI substrate as far as the doped portion of the substrate,
making the sensors on the remaining SOI substrate,
making interconnections between the sensors and the electronic circuit,
releasing the mobile component of the sensors.

Transfer of the SOI substrate and of the substrate provided with the electronic circuit is for example achieved by a cold adhesive bonding method.

In another embodiment manufacturing method according to the present invention, during the step for making the layer provided with the sensors, interconnection pillars are made on one of the faces of said layer, said pillars being connected to the interconnections of said layer by vias, and during the step for making the control and processing layer, interconnection pads connected to the interconnections of the layer by vias are made on one of the faces of said layer.

In an exemplary embodiment, the interconnection pillars are made in the front face of the layer of sensors, and the interconnection pads are made in the front face of the control and processing layer, and during the assembling of the layer of sensors on the control and processing layer, the layer of sensors is transferred onto the control and processing layer according to the "face-to-face" technique. Provision may be made for making the layer of sensors on an SOI substrate, and after the transfer step, for suppressing silicon substrate and depositing a layer of a material resistant to hydrofluoric acid on the insulating material of the SOI substrate instead and in place of the silicon substrate.

SHORT DESCRIPTION OF THE DRAWINGS

The present invention will be better understood by means of the description which follows and of the appended drawings wherein.

DETAILED DISCUSSION OF PARTICULAR EMBODIMENTS

Figure 1:
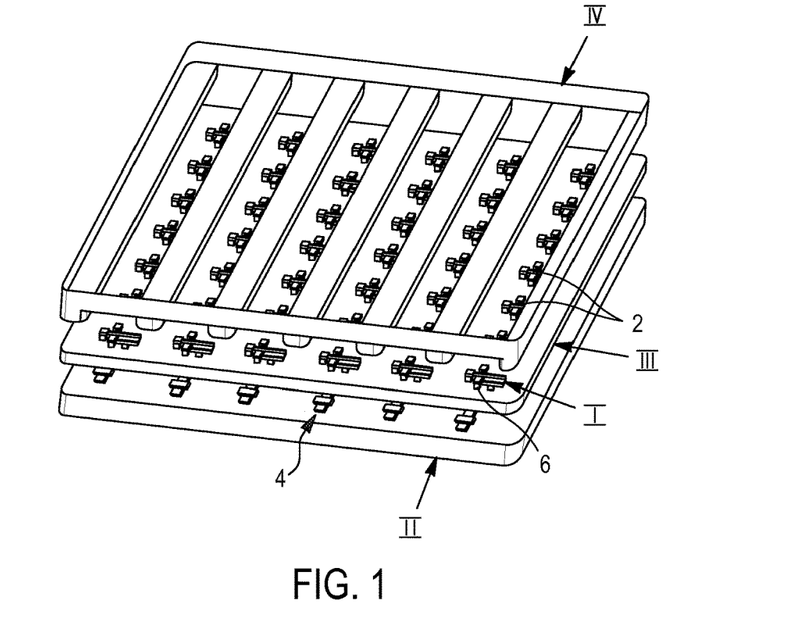
FIG. 1 is an exploded view of an example of an analysis device according to the present invention.
Figure 3:
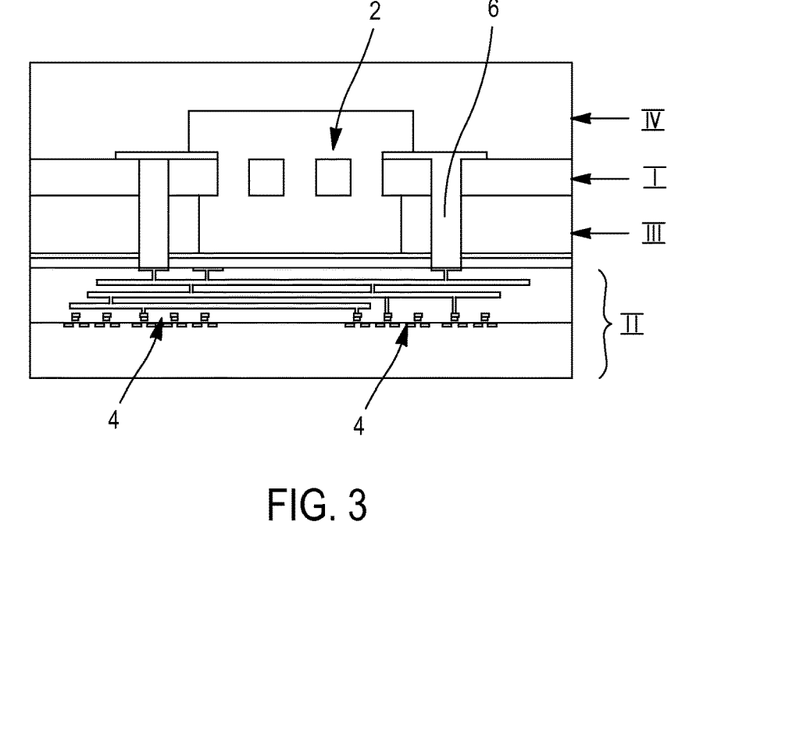
FIG. 3 is a transverse sectional view of the device of FIG. 1.

In FIGS. 1 and 3, an exemplary embodiment of an analysis device according to the present invention may be seen. The analysis device according to the present invention may allow analysis of fluids, gases or liquids, more particularly detection of species by forming a gas chromatography column or measurement of their mass. It may also allow measurement of the forces in a liquid medium, for example cell forces.

The analysis device according to the present invention is an electronic system with three-dimensional integration including several superposed layers.

A first layer designated as I, includes a network of sensors 2 of the MEMS (micro-electromechanical system) type and/or the NEMS (nano-electromechanical system) type. In the illustrated example, the sensors are distributed in lines and in columns. Subsequently in the description, a sensor whether it is MEMS or NEMS will be designated as "sensor". Further, it is well understood that an elementary detector may be formed with several MEMS and/or NEMS micro-sensors.

A second layer II, a so-called electronic layer, includes control and processing means 4 as well as their interconnections. These means 4 are for example formed by transistors, of the CMOS, MOS, biCMOS types etc., with which certain components conventionally used in circuits (capacitors, diodes, resistors, etc. . . . ) may be associated. The level of interconnections of the layer II may also be optionally used for making conventional passive components such as capacitors, inductors, etc. With these means, it is possible to actuate the sensors 2 and to process information transmitted by the sensors 2.

A third layer III ensures the connections between the sensors 2 and the control and processing means 4. It consists of interconnections 6 and of routing of the via type or of the TSV (« Through-Silicon Via) type, etc., in order to electrically connect and address the network of sensors 2 to the control and processing means 4. This third layer III is directly brought back into the rear face of the first layer I of sensors 2 and is interposed between the first I and the second layer II. Alternatively, provision may be made for making a portion of the interconnections in the first layer I of sensors.

Figure 6:
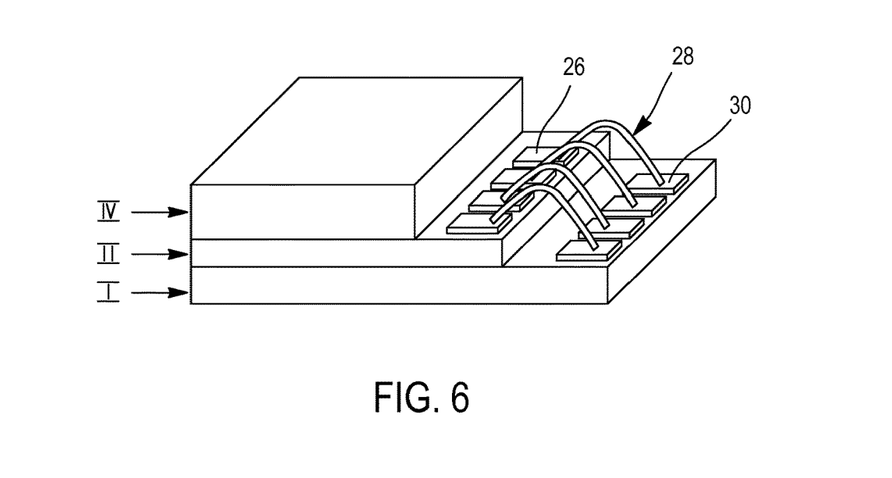
FIG. 6 is a schematic perspective view of an analysis device according to the invention made by wire bonding.

In another alternative, provision may also be made for making the interconnections by wire bonding and not by an intermediate layer, as this is illustrated in FIG. 6.

According to the invention, the analysis device includes a fourth layer IV in the front face of the first layer of sensors I. This layer IV both forms a means for encapsulating the sensors, notably ensuring the protection of the latter toward the outside environment, and ensures controlled distribution of the stimulus or stimuli of the environment to be analyzed on the sensors.

The layer IV, which we shall designate as "distribution layer" in the following, includes means for distributing the stimulus on the sensors 2.

In the case when the environment is a fluid, the distribution means may be of the fluidic type forming a channel for circulation of the fluid on the sensors 2 in a determined way or a plurality of channels bringing the fluid onto each sensor 2.

The distribution means may be of the mechanical type, formed for example by injectors for vaporizing or ionizing the fluid to be analyzed on a given sensor or a group of given sensors.

We shall now describe in detail the different layers of the analysis device.

The first layer I includes a plurality of NEMS and/or MEMS sensors.

In the illustrated example, the sensors are positioned along a network of lines and columns but this distribution is by no means limiting, and for example a circular or spiral arrangement does not depart from the scope of the present invention.

It should be noted that the sensors are not necessarily identical. Further, they may be interconnected as a group.

By applying a plurality of sensors, it is advantageously possible to obtain an image of a given analysis environment: for example a set of different masses, a set of distinct gases, a set of analytes in the liquid phase, imaging of the bolometric type, etc.

Further, the network of sensors allows processing of the information to be performed in parallel. In the case of individually addressed sensors, a large number of measurements may be carried out simultaneously. Thus, instead of having time-multiplexing of the information of a sequential type which is obtained with an analysis device with a single sensor, the invention allows spatial multiplexing of the information.

Furthermore, the robustness of the analysis device is improved relatively to a device with a single sensor, since the malfunction of a sensor does not affect or only very little, the overall operation of the network of sensors.

Moreover, the analysis device according to the invention has improved performances relatively to a device with a single sensor. Indeed, by considering a number N of components having identical structures, and assuming that the noises from each component are uncorrelated, the signal-to-noise (power) ratio of the global system is increased by a factor of N.

Finally, it is possible in a passive or active way, to ensure an identical or synchronized consistent collective response by mechanically and/or electrically coupling the sensors of the network, which allows improvement of the robustness in dispersion.

The sensors may either be all identical or not. As a reminder, an MEMS or NEMS sensor includes a fixed portion and a mobile portion suspended relatively to the fixed portion, the relative displacement of the fixed and mobile portions giving the possibility of obtaining different pieces of information on the outside environment for example. Alternatively, provision may be made for having a network including both MEMS sensors and NEMS sensors.

Figure 4:
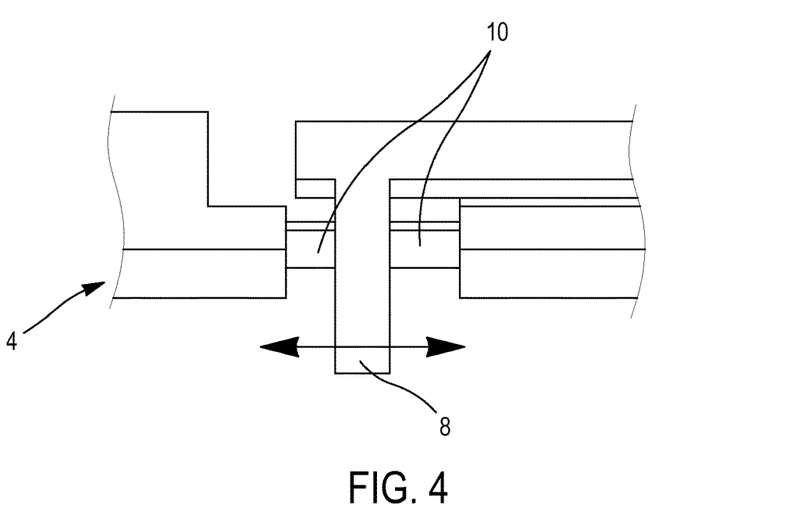
FIG. 4 is a schematic top view of a micro-electromechanical system which may be applied in the present invention.

In FIG. 4, an example of a resonating sensor 4 with a movement in the plane, with electrostatic actuation and piezoresistive detection, may be seen. Piezoresistive detection of the displacement of the mobile portion 8 is for example carried out by means of doped silicon gauges 10.

It is well understood that the sensors may also be of the type with a movement out of the plane, for example a movement in volume, in rotation.

Provision may be made for different actuation means, for example thermo-elastic actuation, electrostatic actuation or piezoelectric actuation, and for different detection means, for example capacitive detection, piezoresitive detection with for example a semiconducting or metal gauge, or further piezoelectric detection.

Figure 2:
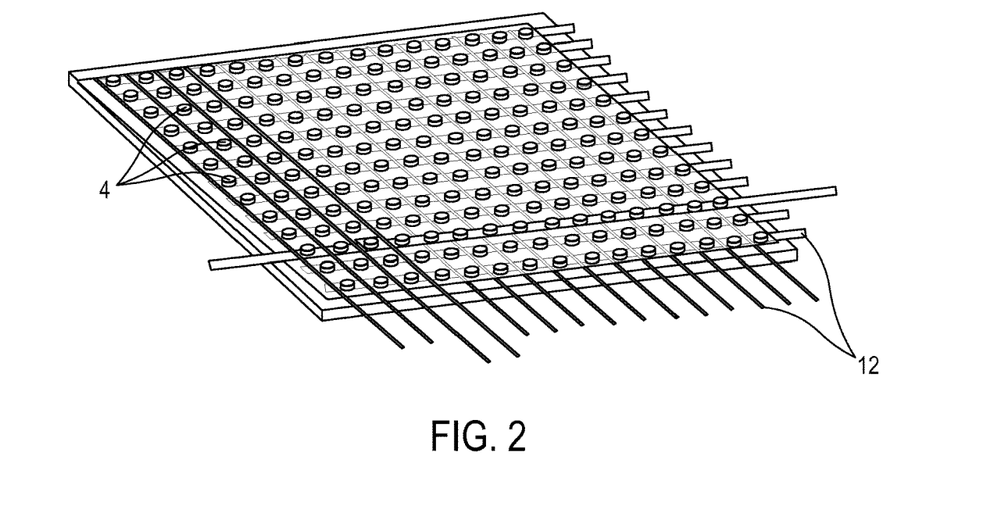
FIG. 2 is a schematic illustration of a network of sensors according to the invention and of lines for addressing said sensors.

In FIG. 2, a schematic illustration of the sensors 4 and of the addressing lines 12 contained in the interconnection layer III may be seen.

The sensors may be addressed collectively, i.e. a single input signal for all the sensors and a single output signal corresponding to the sum of the signals of each sensor, or addressed individually, i.e. each output signal of each sensor is processed by electronics or a portion of the electronics in a dedicated way. Subnetworks may also be made in which the sensors are addressed collectively.

With individual addressing of the sensors, for example by biasing them differently, the frequency change of the sensor may be compensated by adjusting its biasing voltages.

Direct read-out of the compensation allows the detected information to be traced back when the sensors operate as resonating mechanical structures. For example, in the cases when it is desired to measure a mass, addition of mass on the resonant sensors causes a change in the mechanical behavior of the system and a frequency change of the resonator. By measuring the frequency shift, it is possible to trace back the amount of material having interacted with the sensor.

Alternatively, the sensors may be non-resonant structures, then forming force sensors. These sensors may give the possibility of measuring forces in real-time in the liquid medium and notably forces exerted by cells on the mobile portion in order to carry out medical monitoring, such as "pharmascreening" or the measurement of therapeutic effectiveness or the measurement of bacterial virulence or of invasivity of cancer cells, etc.

An MEMS or NEMS sensor used as a force sensor, may measure forces with resolutions of the order of a few tens of picoN in a static measurement and this may be lowered down to a few picoN for analysis frequencies of a few hundred to a few thousand Hz.

As this will be seen subsequently, according to the application of the analysis device, provision may be made for functionalizing the sensors by means of a chemical layer, in order to improve their specificity toward analytes to be measured.

The second layer II includes control and processing means intended for actuating, controlling and measuring the electromechanical behavior of the sensors.

In the applications where the sensors form resonators, with the means of the electronic layer II it is possible to set the sensors into resonance and to accomplish dynamic tracking, i.e. in real time, of the time-dependent frequency change of the sensors.

For example, the electronic layer II may include measurement architectures mainly based on oscillators and/or on approaches of the phase locked loop or PLL type.

For static or quasi-static low frequency applications, the control and processing means 4 of the electronic layer II carry out real-time measurement of the mechanical displacement of the sensors II.

In an exemplary embodiment, provision may be made for dividing the electronic layer II into two interconnected sublayers, for example by means of vias or vias through the silicon or TSV (Through-Silicon Via) etc.

For example, a first sublayer includes near-pixel basic electronics for analog preprocessing of each sensor (notably analog/digital conversion, analog compression before conversion . . . ). A second sublayer includes electronics performing the whole digital processing of the information, for example by means of digital processors (shaping the output signals in a standardized communications protocol of the PCI, USB type etc. . . . ).

Further, the control and processing means of the electronic layer may be programmable and therefore reconfigured according to needs, for example in order to combat dispersions, in order to carry out adjustment to the working environment in an optimal way or in order to perform other additional functions such as temperature compensations, etc.

The interconnection layer III, as this was explained earlier, has the function of achieving the electric interface between the sensors 2 and the control and processing means 4. With this layer III, it is possible not to resort to connection techniques of the wire-bonding type, which limits the number of sensors of the network.

The layer III for example includes vias, vias through silicon or TSVs, may be made by "oxide bonding", i.e. by molecular bonding between two oxide layers or other materials allowing molecular bonding and including contact recovery. An interconnection layer III may then be made, having a large integration level relatively to its size, which allows an increase in the density of the networks of sensors.

Further, the layer III also allows adjustment of the sizes between the layer of sensors I and the electronic layer II in order to optimize assembling and costs. Provision may be made for making the layers I and II with different methods depending on their cost and for interfacing them by "wire bonding" and TSV.

The fourth layer IV forms both an encapsulation and distribution layer for the stimulus or stimuli of the environment to be analyzed. The latter layer is added onto the first layer I including sensors.

The layer IV according to the present invention may be of different types depending on the sought application for the analysis device.

In the case when the environment is a fluid, this distribution layer may be chemically functionalized depending on the selected applications. Further, the distribution layer may be electrically controllable. Provision may be made for having the relevant layer contain valves, for example controlled in order to either let through the fluid(s) or not and to thereby direct them suitably, in a controlled way.

The distribution layer IV may also include filtering means for sorting out the species, for example in solution. These means may for example be of the grid type. For example the filtering means include pores with adjustable size, only letting through molecules with a given maximum size.

In a first application, the analysis device according to the present invention may form a mass spectrometer. The distribution layer IV then includes injection and ionization means allowing projection of a mixture of substances to be analyzed, for example proteins on the network of sensors. The injection means are for example mechanical components of the injector type or means capable of forming a spray.

The injector may be of the electrospray ionization (ESI) type ensuring dispersion of a liquid as electrically charged droplets.

The injectors may be mechanical, similar to inkjet printing nozzles. In this case, they are dimensioned so as to allow dispersion of droplets containing an adequate amount of molecules, for example proteins, while promoting spatial separation of the molecules without degrading them.

Figure 8:
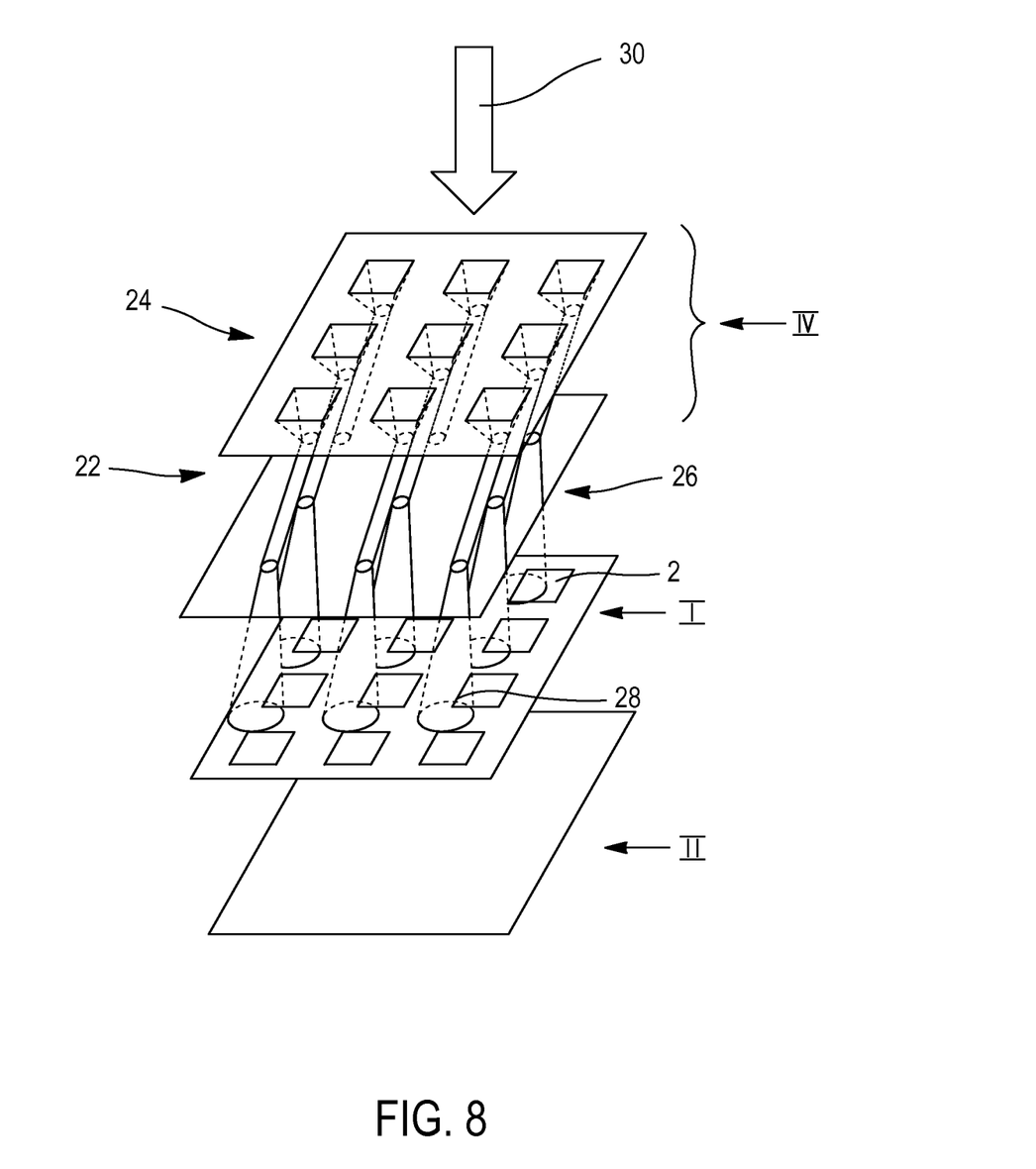
FIG. 8 is an exploded view of a schematic illustration of an embodiment device according to the present invention including injectors.

In FIG. 8, a schematically illustrated exemplary embodiment of such a device may be seen. In this exemplary embodiment, the distribution means include injectors 22 formed by a network of biased tips pierced with holes, a biased counter-electrode 26 including holes, the counter-electrode 26 being positioned between the network of tips 24 and the layer of sensors I. The injectors are substantially aligned with the sensors of the layer I. Dispersion cones 28 for the injected gas on the sensors, are also illustrated. The inflow of gas is symbolized by the arrow 30.

With the arrangement of injectors directly above the sensors, it is possible to avoid too large spatial dispersions of molecules, whether they are ionized or not, and to better focus the species of interest, which improves the detection yield.

The proximity of the network of sensors and of the injection system allows reduction of on-line losses and with the high mass sensitivity of the MEMS or NEMS sensors it is possible to have an electric signal identical with those of the other sensors. Therefore, the ionization yield may be lower as compared with less sensitive and more remote detectors, which reduces the constraints on the yield of the injectors, notably when it ionizes the molecules to be analyzed.

Analysis times are also reduced.

In the case of a mass spectrometer, the vacuum is applied between the distribution layer and the sensors.

In another embodiment, the sensors may also be used for measuring force in order to detect molecules contained in a liquid, for example cells, such as proteins. As this was indicated earlier, NEMS sensors allow the measurement of forces of the order of a hundred pN (piconewtons).

In this case, the distribution layer includes channels for example bringing the different cells with their adequate survival environment directly onto each micro-electromechanical detector of the network. By measuring the force applied by each cell on the mobile portion in the sensors in real time, it is possible to determine its characteristics and the change in mechanical behavior of each cell depending on the type/amount of molecules injected into said cells. This thus allows characterization/differentiation of for example cancer cells, evaluation of their invasivity and their capability of metastasizing. This also potentially allows measurement of the toxicity of certain pharmacological molecules on the cells or evaluation of the effectiveness (and of the possible action mechanisms) of therapeutic treatments on «diseased» cells. The analysis yield is then increased since it is possible to carry out force measurements on all the sensors simultaneously. For example, the distribution layer IV includes a plurality of channels connected to a fluid supply, each channel arriving opposite to a sensor.

Figure 5A:
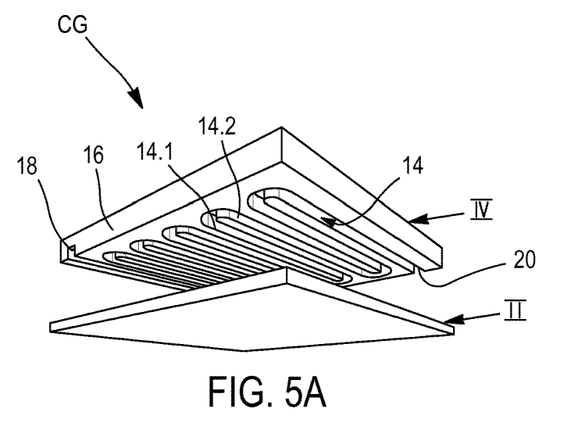
FIGS. 5A and 5B are exploded views of a particularly interesting example of an analysis device according to the present invention according to two different views.
Figure 5B:
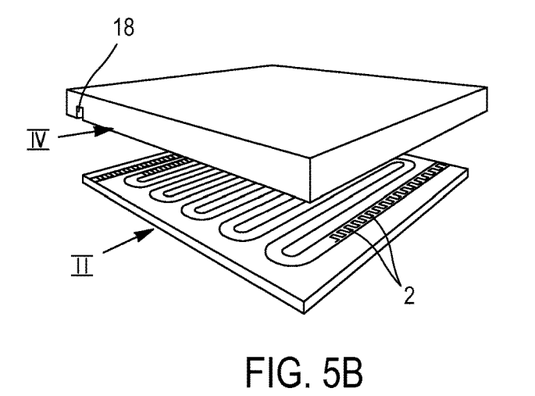

The analysis device according to the present invention may in a particularly advantageous way form a gas chromatography GC micro-column illustrated in FIGS. 5A and 5B. The distribution layer IV then includes one or more grooves 14. The layout of the groove(s) 14 follows the arrangement of the sensors 2, so that a column is available, one face of which is provided with sensors 2 regularly distributed in said column, along the direction of flow of the fluid.

For example, the groove(s) measure(s) from a few tens of pm to a few hundred pm in depth and a few tens of pm to a few hundred pm in width. For example they are etched in a silicon substrate by conventional microelectronic techniques associating photolithographic and deep etching steps. This substrate may for example be transferred by molecular sealing or anodic sealing onto the layer of sensors I. Firmly attaching both layers by means of an adhesive deposited by screen-printing may also be contemplated.

On a surface of a few square centimeters, a column may thereby be made:
  the section of which is determined by the etching depth and the width of the etching. Each of these dimensions may vary from about ten to a few hundred microns,
  the length may range from a few tens of centimeters to one or more meters for example two meters.

In FIGS. 5A and 5B, the groove 10 includes parallel outward bound 14.1 and inward bound 14.2 sections etched in a substrate 16. The channel includes an end for the supply of fluid to be analyzed 18 and an end 20 for discharging said fluid.

Said provision may be made for associating with the microcolumn a micro-preconcentrator (not shown) at the inlet of the microcolumn.

Alternatively, the chromatography column may be wound on itself, forming two spirals nested in each other for example.

Further, this distribution layer may be chemically functionalized: the grooves etched in the silicon may be covered with a stationary phase, formed for example with PDMS (polydimethylsiloxane), silanes or other polymers.

Further, the sensors are advantageously functionalized with an adsorbing material, for example a sensitive polymer, having chemical affinity with the compounds of the mixture to be analyzed. In the presence of a chemical compound, a certain amount of this compound will be adsorbed on the sensitive layer and will generate a signal on the sensor. The adsorbing material(s) may either be identical with the stationary phase(s) or different.

The network of sensors of layer I includes at least a sufficient number of detectors regularly spaced out so that their spacing is less than half of the width of a peak. For a given column, the average width of a peak may be estimated by the "height equivalent of a theoretical plate". In practice, it is advantageous to have detectors spaced out by about one millimeter, i.e. about 1,000 for a column of one meter.

By means of the chromatography column according to the invention, it is possible to determine the average velocity of each compound between two successive detectors, a possibly variable velocity depending on the position of the compound in the column. It is therefore possible to reconstruct a two-dimensional space-time map of the concentration of compounds in the column.

Moreover, by means of the chromatography column according to the invention, a second sample may be introduced before all the constituents of the first sample have exited. Depending on the complexity of the samples, characterized by the number of constituents and corresponding peaks in the column, a sufficient number of detectors may be available for tracking each constituent and detecting the constituents of the second sample, the velocity of which is greater than that of the constituents of the first sample, so that there is no longer any uncertainty. For samples of arbitrary complexity, it is sufficient to have the detectors with a density such that their spacing is less than the half width of a peak.

It is possible to connect several columns according to the invention in series, allowing an increase in the separation capacities of the analysis system.

We shall now describe exemplary methods for making an analysis device according to the present invention.

The analysis device according to the present invention is of the three-dimensional integrated circuit type ensuring great compactness.

According to a first embodiment method, the distribution layer is made in a substrate in a semiconducting material, such as silicon, by etching the substrate so as to form microchannels in the case of a gas chromatography micro-column. Moreover the layer of sensors I and the electronic layer II are made.

The analysis device according to the invention obtained by this method may be seen in FIG. 6.

The distribution layer IV is adhesively bonded onto the layer I of sensors, while leaving clear an area of pads 26 connected to the sensors.

The thereby formed assembly is then adhesively bonded above or beside the electronic layer II.

Wire bonding 28 is then carried out for connecting the pads 26 of the layer I of sensors to the pads 30 of the electronic layer II.

This method is particularly of interest when the number of sensors is limited, for example to less than 100.

According to another embodiment method illustrated in FIGS. 7A-7E, the TSV ("Through Silicon Via") principle is used which consists of connecting together two electronic circuits by means of through-vias. In the following, we shall call a top circuit the layer I including the MEMS and/or NEMS and its interconnections and a bottom circuit the electronic circuit II forming the CMOS control circuit.

The method includes the following steps:
  Making the top circuit I,
  Making interconnection pillars on the top circuit,
  Making the bottom circuit II and its interconnections,
  Transferring the top circuit I onto the bottom circuit II,
  Releasing the MEMS and/or NEMS sensors.

We shall now describe these different steps above in detail.

Figure 7A:
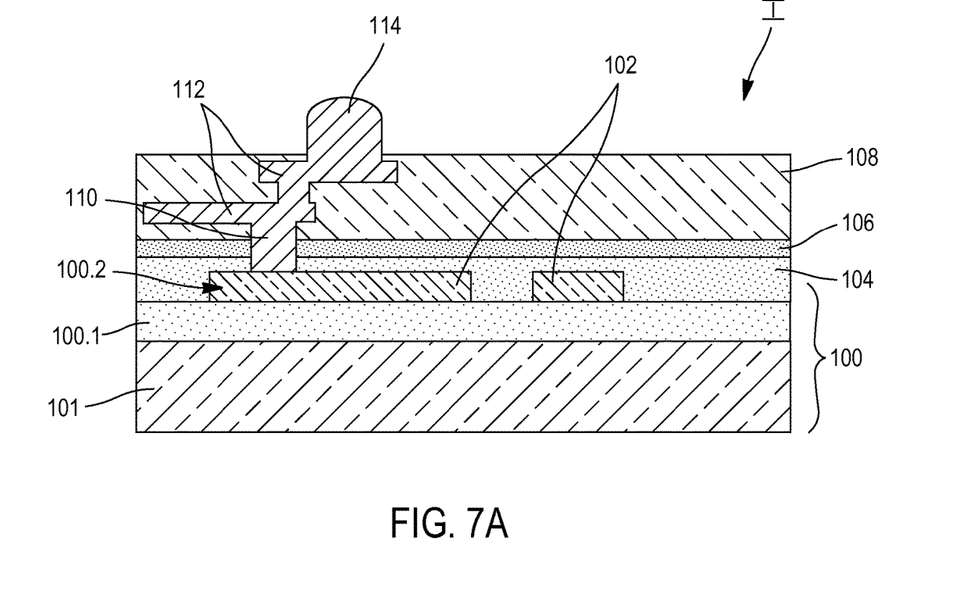
FIGS. 7A-7E are schematic illustrations of the different steps of an exemplary method for making an analysis device according to the present invention.

In order to make the top circuit I, an SOI substrate 100 deposited on a silicon substrate 101 is for example used. The SOI substrate includes an insulating material, for example SiO$_2$, layer 100.1, and a layer 100.2 of silicon or of a semiconducting material deposited on the insulating material layer 100.1. Doping of an SOI substrate 100 is carried out, for example of the P type. A step for lithography and etching of the layer 100.2 for forming patterns 102 then takes place.

An insulating material layer 104, for example in SiO$_2$, in SiO, or in any other insulating material, conventionally used in microelectronics for the back-end is then deposited on the patterns 102.

A step for planarization of the layer 104 is then carried out, for example by mechanochemical polishing or CMP (Chemical Mechanical Polishing) or vapor-phase polishing.

A stop layer 106 involved during the release of the NEMS and/or MEMS sensors is then deposited. The MEMS and/or NEMS release is for example achieved by means of hydrofluoric acid. For this stop layer, any material which is not or only very slightly attacked by HF as compared with interconnection insulators used for the layer 104 is therefore selected. This may for example be a nitride layer (Si$_3$N$_4$, SiN . . . ), or HfO$_2$.

An insulator layer 108 is then deposited on the stop layer 106.

Vias 110 are then made through the insulator layers 104 and 108 and the stop layer 106 as far as the patterns 102.

After a step of possible doping and silicidation of the contact bottoms, the vias 110 are for example filled with tungsten and/or copper and/or TiN . . . , etc.

A step for planarization of the filling takes place. One or more interconnection levels 112 are then made above the vias on the insulator layer 108.

During a following step, interconnection pillars 114 are made on the top circuit between the top circuit I and the bottom circuit II, and a step for thinning the silicon substrate 101 is performed.

The bottom circuit is illustrated in FIG. 7A.

Next, a step for thinning the silicon layer of the SOI 100 is carried out.

The bottom circuit II is made according to a standard method.

Figure 7B:
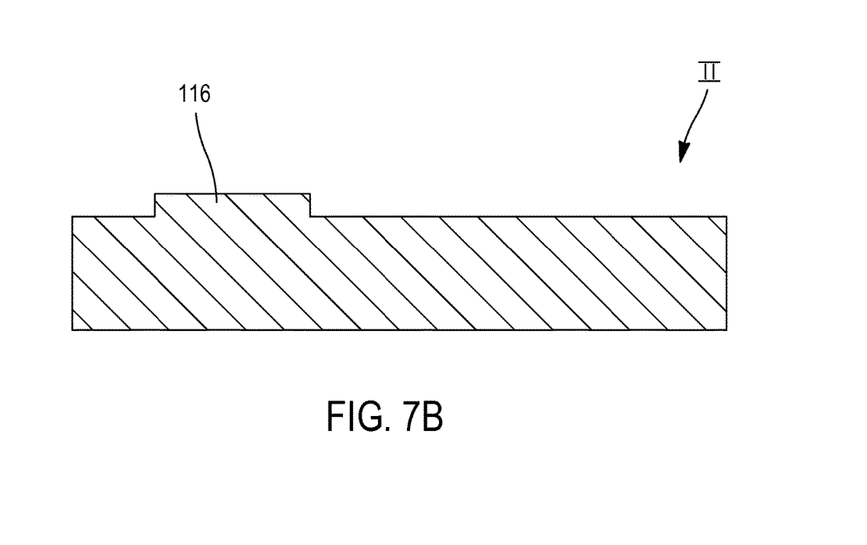

Copper pads 116 are then made in the front face of the top circuit II for interconnection with the copper interconnection pillars 114. The bottom circuit provided with pads 116 is illustrated in FIG. 7B.

Figure 7C:
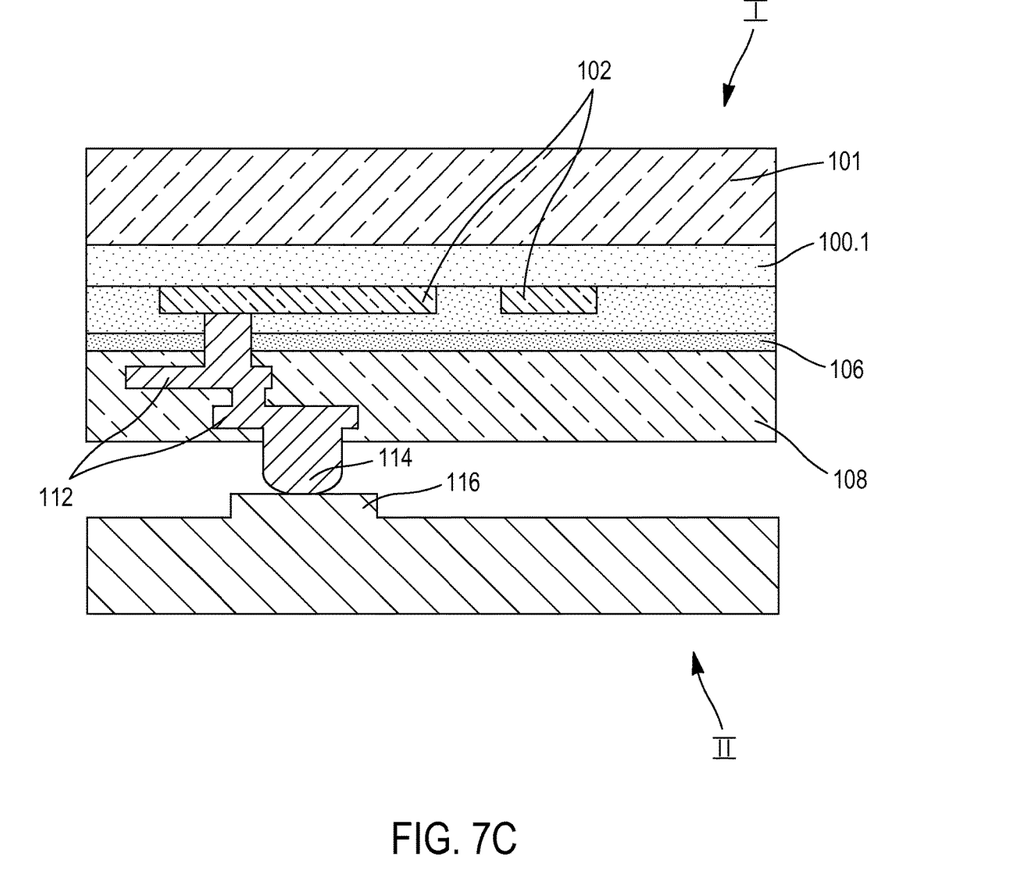

During a following step, the top circuit I is transferred onto the bottom circuit II while aligning the interconnection pillars 108 and the interconnection pads 116 (FIG. 7C). Both circuits are adhesively bonded. In the illustrated example, the top circuit I is transferred onto the bottom circuit II according to the face-to-face technique, for this the bottom circuit is turned over. Alternatively, it may be transferred according to the back-to-face technique.

Advantageously, a material is provided between the top circuit I and the bottom circuit II, with which the empty space may be suppressed and good adhesion may be ensured. The material is for example a resin or a polymer deposited by the spin-off technique, or an oxide deposited and then planarized by CMP, as this is for example described in the document Bioh Kim; Thorsten, M.; Wimplinger, M.; Lindner, P; "*Advanced Wafer Bonding Solutions for TSV Integration with Thin Wafers*" IEEE International Conference on 3D System Integration, 2009.

Figure 7D:
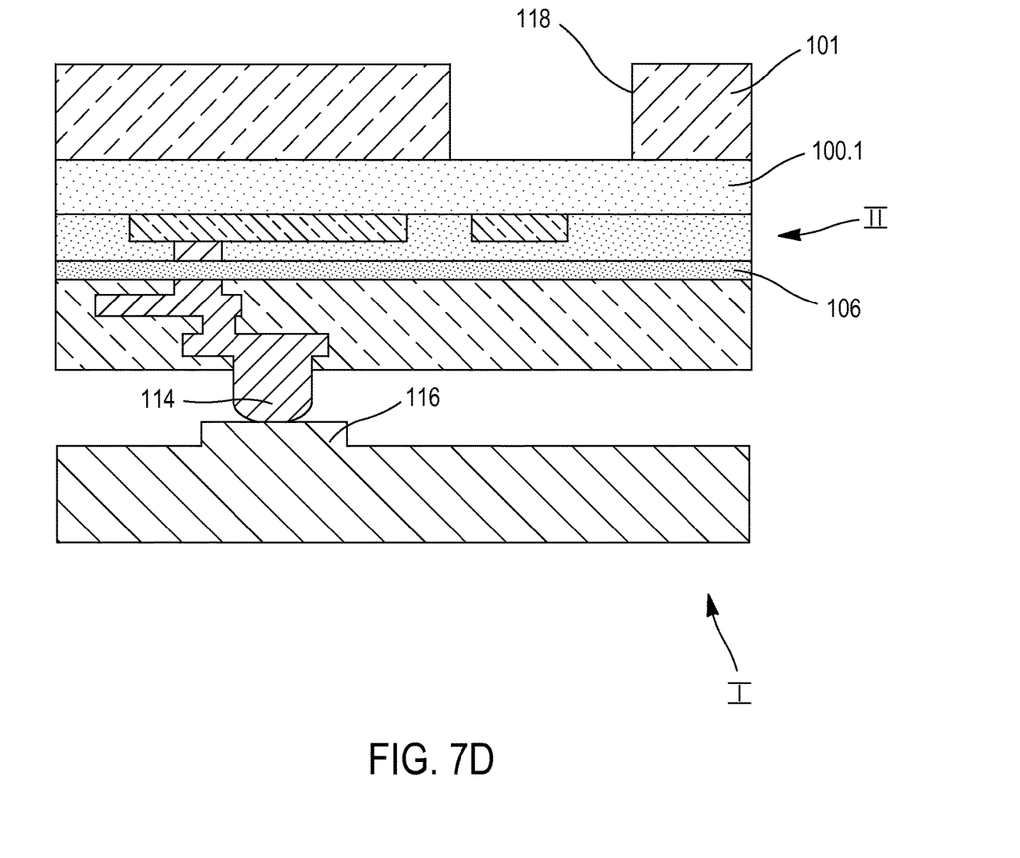

A step for lithography and etching of cavities 118 in the silicon layer of the top circuit is then carried out, in the rear face of the top circuit at the beginning of the method. This etching may be achieved for example by anisotropic plasma etching or by chemical etching with TMAH (tetramethyl-ammonium hydroxide). Etching of the silicon is stopped in the insulator layer 100.1. These cavities 118 are made above the NEMS or MEMS portions which one intends to release (FIG. 7D).

Figure 7E:
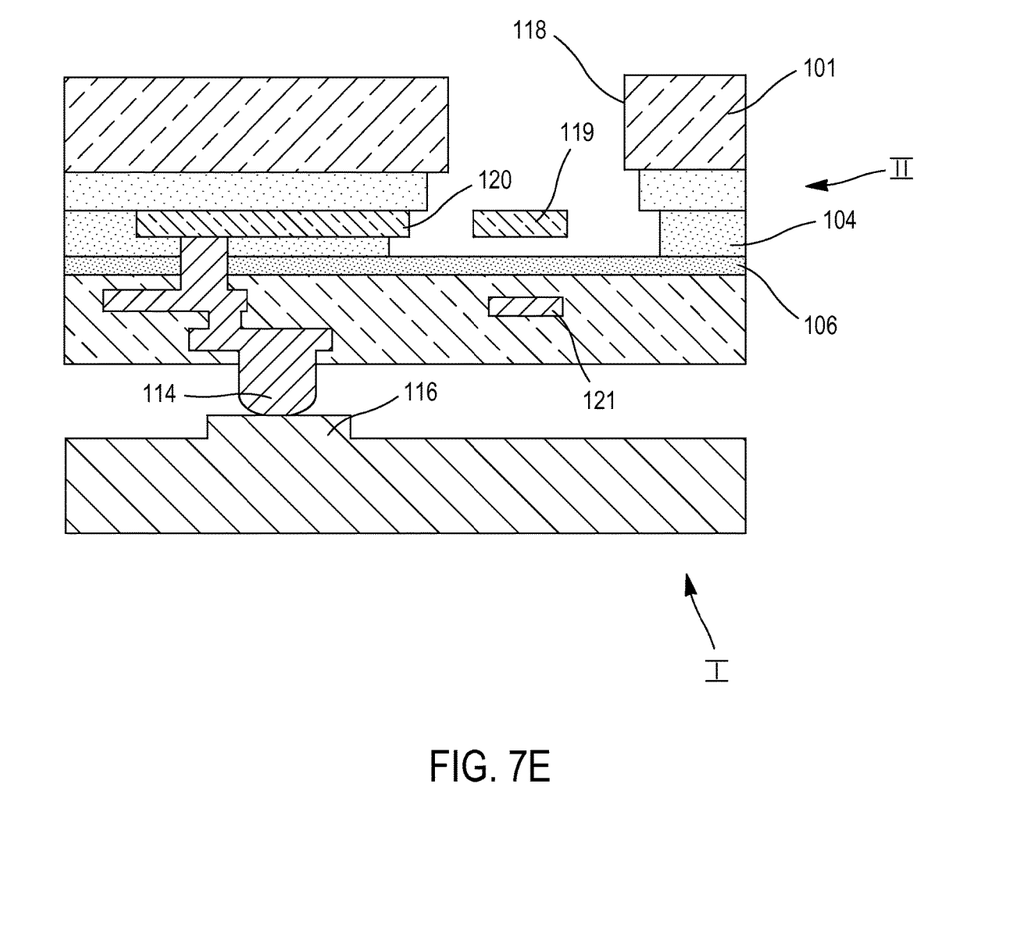

During a following step, the mobile portion 119 of the MEMS or NEMS is released by etching the insulator layer 100.1 and the interconnection insulator layer 104 of the NEMS with hydrofluoric acid vapor (FIG. 7E).

The distribution layer IV (not shown) is then transferred onto the layer I, for example by adhesive bonding.

Alternatively, after the transfer of the top circuit onto the bottom circuit in a face-to-face configuration, provision may be made for completely removing the silicon substrate 101 by chemical etching with TMAH or by plasma, this etching being stopped on the insulator layer 100.1. Deposition on the insulator layer 100.1 of a layer of a material resistant to hydrofluoric acid for example nitride or amorphous silicon, is then carried out. This layer may have a thickness of about 50 nm.

This layer is then etched and the MEMS and/or NEMS sensors are released with hydrofluoric acid.

This alternative has the advantage of having at the end of the method a thinner layer than the silicon substrate 101 which has been suppressed, which less perturbs the advance of the gases towards the MEMS and/or NEMS sensors, for example in biological applications.

NEMS and/or MEMS control may be achieved either by the electrode 120 in the plane, or by an interconnection 121 located under the mobile portion of the MEMS or NEMS (FIG. 7E).

Alternatively, the bottom circuit II may form an interposer, i.e. an intermediate circuit between the top circuit I and another circuit, positioned under the bottom circuit and interconnected with the bottom circuit II.

The analysis device according to the present invention may be obtained by a third embodiment method with which very high integration density may be obtained.

The method includes the steps:

making a CMOS, MOS, biCMOS circuit, etc. on a substrate with its interconnections.

doping a thin SOI substrate, the doping preferentially being of the P type and thermally activating the dopants, for example between 900° C. and 1,050° C. The SOI substrate may also be replaced with an epitaxied substrate Si/SiGe/Si. SiGe then replaces the SiO$_2$ insulator as a sacrificial layer.

depositing above the SOI substrate a layer stopping hydrofluoric acid for example, such as SiN or SI$_3$N$_4$ or HfO$_2$ . . . , covered with a layer promoting adhesive bonding such as SiO.

adhesively bonding both substrates face-to-face for example by a cold adhesive bonding method such as the one described in the document "*Setting up 3D sequential integration for back-illuminated CMOS image sensors with highly miniaturized pixels with low temperature fully depleted SOI transistors*" Coudrain, P.; Batude, P.; Gagnard, X.; Leyris, C.; Ricq, S.; Vinet, et al." *Electron Devices Meeting, IEDM* 2008. pp.1-4, 15-17). The adhesive bonding carried out is for example oxide/oxide hydrophilic bonding. A silicon oxide, for example of the high density plasma (HDP) type is deposited on the supporting wafer and on the transferred wafer. The topography of the dielectric on the supporting wafer is suppressed so as to be able to place two planar surfaces face-to-face. Adhesive bonding is carried out at room temperature. The annealing for solidifying the interface (for example 200° C., 1 hour) allows generation of covalent bonds between both oxides. Thinning of the SOI substrate is obtained by mechanical abrasion and then by selective etching at the stop layer. For example, this may be chemical etching (TMAH: tetramethylammonium hydroxide) with stoppage on the buried oxide. This oxide will be selectively removed relatively to Si, leaving the thin silicon layer adhesively bonded to the top of the lower transistor. In this case, the insulator of the SOI substrate is SiGe instead of $SiO_2$, the chemical etching step by TMAH may be replaced with plasma etching which is stopped in the SiGe layer. The SiGe layer may then be removed selectively relatively to the Si layer, for example by ex situ isotropic plasma based on SF4.

making the NEMS sensors by lithography and etching in a way known to one skilled in the art, making the interconnections between the layer of NEMS sensors and the pads of the circuit below. Jutting-out AlSi pads may be made as used in a known way in NEMS, releasing the NEMS or MEMS sensors with hydrofluoric acid as a vapor with stoppage on the stop layer deposited on the SOI substrate.

adhesively bonding the distribution layer made beforehand by etching microchannels in the case of a gas chromatography column.

By means of the invention, an analysis device was made, provided with a network of MEMS or NEMS sensors, having great compactness and providing a certain number of advantages.

In certain applications, for example as a mass spectrometer or a force sensor for analysis of molecules, the analysis yield is substantially increased, since it allows a large number of measurements to be carried out simultaneously.

It further allows a gas chromatography microcolumn to be made providing great compactness, with this column it is possible to be informed on the average velocity of each species and to separate the latter in a reliable way.

The invention claimed is:

1. A device for analyzing a fluid, comprising:
only one sensor layer including a plurality of sensors of MEMS or NEMS to generate information associated with a chemical composition of the fluid, each sensor of the plurality of sensors including at least one mobile component that reacts to one or more characteristic stimuli of the fluid, the mobile component being suspended relatively to a fixed component, and each mobile component configured to move independently from mobile components of other sensors of the plurality of sensors;
a processing circuitry layer including processing circuitry configured to process the information transmitted by the sensors, the processing circuitry being electrically connected to the sensors; and
a distribution layer positioned on the only one sensor layer on a side of a face including the sensors, the distribution layer including a distributor to spatially and temporally distribute stimulus or stimuli to the sensors, the distributor comprising a plurality of channels to bring onto each sensor or group of sensors independently the stimulus or the stimuli simultaneously or quasi simultaneously or one channel to bring onto each sensor or group of sensors the stimulus or the stimuli successively, the only one sensor layer, the processing circuitry layer, and the distribution layer being arranged in a stacked fashion with the only one sensor layer being between the distribution layer and the processing circuitry layer.

2. The analysis device according to claim 1, wherein the distributor including a plurality of channels, one end of which, as an inlet end, is configured to be connected to a supply of fluid to be analyzed.

3. The analysis device according to claim 2, wherein the sensors form resonators, and wherein the distributor includes an injector to inject or an ionizer to ionize the fluid on each sensor or a group of sensors, the plurality of channels including a second end connected to the injector or ionizer, the injector facing the sensor of the group or sensors and injecting or projecting the stimulus or stimuli directly on the sensor or the group of sensors.

4. The analysis device according to claim 3, wherein the injector includes at least one injector of electrospray ionization.

5. The analysis device according to claim 1, wherein the distribution layer includes at least one filter to filter certain compounds contained in the fluid.

6. The analysis device according to claim 1, wherein the distributor includes a plurality of channels configured to deliver fluid containing cells to each of the sensors, a second outlet end of each of the channels opening out above a sensor or a group of sensors, the sensors forming sensors of forces applied by the cells on the mobile component of the sensors.

7. The analysis device according to claim 1, wherein the distributor including a channel forming a gas chromatography microcolumn.

8. The analysis device according to claim 7, wherein the channel of the distributor includes at least one groove made in the distribution layer, an open end of the groove covering a succession of sensors, so the fluid circulating in the groove comes into contact with the succession of sensors.

9. The analysis device according to the claim 8, wherein the at least one groove includes at least one stationary phase.

10. The analysis device according to claim 7, wherein the sensors are chemically functionalized by depositing at least one material providing a certain affinity with species to be separated from the fluid to be analyzed.

11. The analysis device according to claim 7, wherein a gap between the sensors is less than half a width of a detection peak.

12. The analysis device according to claim 1, further comprising an interconnection layer between the only one sensor layer and the processing circuitry layer, the interconnection layer electrically connecting the sensors to the processing circuitry.

13. The analysis device according to claim 1, wherein the processing circuitry layer is divided into interconnected first and second sublayers, the first sublayer including near-pixel basic electronics for analog preprocessing of each sensor, and the second sublayer including electronics configured to achieve digital processing of the information.

14. The analysis device according to claim 1, wherein a top surface of the only one sensor layer faces a bottom surface of the distribution layer, and a bottom surface of the only one sensor layer faces a top surface of the processing circuitry layer.

15. The analysis device according to claim 1, wherein the distribution layer is adhesively bonded onto the only one sensor layer, and the processing circuitry layer is adhesively bonded to the only one sensor layer.

16. The analysis device according to claim 1, wherein the processing circuitry layer includes a plurality of processing circuitry disposed thereon.

17. A device for analyzing a fluid, comprising:
only one sensor layer including a plurality of sensors of MEMS or NEMS to generate information associated with a chemical composition of the fluid, each sensor of the plurality of sensors including at least one mobile component that reacts to one or more characteristic stimuli of the fluid, the mobile component being suspended relatively to a fixed component, and each mobile component configured to move independently from mobile components of other sensors of the plurality of sensors;
a processing circuitry layer including processing circuitry configured to process the information transmitted by the sensors, the processing circuitry being electrically connected to the sensors; and
a distribution layer positioned on the only one sensor layer on a side of a face including the sensors, the distribution layer including a distributor to spatially and temporally distribute stimulus or stimuli to the sensors, the distributor including one channel to bring onto each sensor or group of sensors the stimulus or the stimuli successively, the only one sensor layer, the processing circuitry layer, and the distribution layer being arranged in a stacked fashion with the only one sensor layer being between the distribution layer and the processing circuitry layer.

18. The analysis device according to claim 17, wherein a top surface of the only one sensor layer faces a bottom surface of the distribution layer, and a bottom surface of the only one sensor layer faces a top surface of the processing circuitry layer and wherein a bottom of the channel is made by the top surface of the only one sensor layer, such that the sensors are located in the channel.

19. A device for analyzing a fluid, comprising:
only one sensor layer including a plurality of sensors of MEMS or NEMS to generate information associated with a chemical composition of the fluid, each sensor of the plurality of sensors including at least one mobile component that reacts to one or more characteristic stimuli of the fluid, the mobile component being suspended relatively to a fixed component, and each mobile component configured to move independently from mobile components of other sensors of the plurality of sensors;
a processing circuitry layer including processing circuitry configured to process the information transmitted by the sensors, the processing circuitry being electrically connected to the sensors; and
a distribution layer positioned on the only one sensor layer on a side of a face including the sensors, the distribution layer including a distributor to spatially and temporally distribute stimulus or stimuli to the sensors, the distributor including a plurality of channels to bring onto each sensor or group of sensors independently the stimulus or the stimuli simultaneously or quasi simultaneously, the only one sensor layer, the processing circuitry layer, and the distribution layer being arranged in a stacked fashion with the only one sensor layer being between the distribution layer and the processing circuitry layer.

20. The analysis device according to claim 19, wherein a top surface of the only one sensor layer faces a bottom surface of the distribution layer such that the plurality of channels output to the sensor or the group of sensors, and a bottom surface of the only one sensor layer faces a top surface of the processing circuitry layer.

21. A device for analyzing a fluid, comprising:
only one sensor layer including a plurality of sensors of MEMS or NEMS to generate information associated with a chemical composition of the fluid, each sensor of the plurality of sensors including at least one mobile component that reacts to one or more characteristic stimuli of the fluid, the mobile component being suspended relatively to a fixed component, and each mobile component configured to move independently from mobile components of other sensors of the plurality of sensors, the plurality of sensors comprising at least a first sensor and at least a second sensor, the at least first sensor being different from the at least second sensor;
a processing circuitry layer including processing circuitry configured to process the information transmitted by the sensors, the processing circuitry being electrically connected to the sensors; and
a distribution layer positioned on the only one sensor layer on a side of a face including the sensors, the distribution layer including a distributor to spatially and temporally distribute stimulus or stimuli to the sensors, the distributor comprising at least a first channel and a second channel, the first channel bringing onto the at least first sensor the stimulus or the stimuli and the second sensor bringing onto the at least second sensor the stimulus or the stimuli, the stimulus or the stimuli acting simultaneously or quasi simultaneously on the at least first sensor and the at least second sensor, or one channel to bring onto the at least first sensor and the at least second sensor the stimulus or the stimuli successively, the only one sensor layer, the processing circuitry layer, and the distribution layer being arranged in a stacked fashion with the only one sensor layer being between the distribution layer and the processing circuitry layer.

* * * * *